(12) United States Patent
Kanters et al.

(10) Patent No.: US 7,404,880 B2
(45) Date of Patent: Jul. 29, 2008

(54) SENSOR ELEMENT

(75) Inventors: Johannes Kanters, Stuttgart (DE);
Lothar Diehl, Gerlingen (DE); Stefan Rodewald, Ditzingen (DE)

(73) Assignee: Robert Bosch GmbH, Stuttgart (DE)

( * ) Notice: Subject to any disclaimer, the term of this patent is extended or adjusted under 35 U.S.C. 154(b) by 637 days.

(21) Appl. No.: 10/515,619

(22) PCT Filed: May 20, 2003

(86) PCT No.: PCT/DE03/01626

§ 371 (c)(1),
(2), (4) Date: Jun. 23, 2005

(87) PCT Pub. No.: WO03/104790

PCT Pub. Date: Dec. 18, 2003

(65) Prior Publication Data

US 2005/0241936 A1    Nov. 3, 2005

(30) Foreign Application Priority Data

Jun. 6, 2002   (DE) .................................. 102 25 149

(51) Int. Cl.
*G01N 27/26*    (2006.01)
*H05B 1/02*     (2006.01)

(52) U.S. Cl. ................ 204/426; 204/400; 204/408; 204/424; 219/497; 219/499; 73/1.02

(58) Field of Classification Search ................ 204/424, 204/426; 219/497, 499, 504, 505
See application file for complete search history.

(56) References Cited

U.S. PATENT DOCUMENTS

| 4,650,560 | A |   | 3/1987 | Ueno |          |
|-----------|---|---|--------|------|----------|
| 4,814,059 | A | * | 3/1989 | Nishizawa et al. | 204/406 |
| 4,851,103 | A | * | 7/1989 | Usami et al. | 204/406 |
| 5,516,410 | A | * | 5/1996 | Schneider et al. | 204/426 |
| 6,888,109 | B2| * | 5/2005 | Heimann et al. | 219/484 |
| 2005/0160793 | A1 | * | 7/2005 | Schumann et al. | 73/31.05 |

FOREIGN PATENT DOCUMENTS

| DE | 19746516 | 5/1999 |
| DE | 19834276 | 2/2000 |
| DE | 19853601 | 5/2000 |
| DE | 19857470 | 6/2000 |
| DE | 19932545 | 1/2001 |
| DE | 10042000 | 5/2002 |
| DE | 10054828 | 5/2002 |
| DE | 10058643 | 6/2002 |

\* cited by examiner

*Primary Examiner*—Patrick Ryan
*Assistant Examiner*—Kourtney R Salzman
(74) *Attorney, Agent, or Firm*—Kenyon & Kenyon LLP

(57) ABSTRACT

A layered sensor element used in a gas measuring sensor for measuring a physical property of a measuring gas, preferably for determining the temperature of the measuring gas or the concentration of a component of the measuring gas. The sensor element contains a wave-form heater, which is embedded in a porous heater insulation. At least one separating element having a lower porosity than the porous heater insulation is provided between two adjacent sections of the wave-form heater.

16 Claims, 1 Drawing Sheet

SENSOR ELEMENT

BACKGROUND INFORMATION

German Patent Application No. DE 198 34 276, for example, describes a sensor element. The planar, elongated sensor element contains an electrochemical cell having a first and a second electrode, as well as a solid electrolyte located between the first and the second electrode. Furthermore, the sensor element contains a wave-form heater situated between two insulation layers.

The heater and the layers adjacent to the heater are exposed during operation to high mechanical stresses, which result from temperature fluctuations and the temperature gradients occurring within the layers. To prevent cracks, for example, from occurring in the insulation layers due to these stresses, the insulation layers have a porous design and therefore have adequate elasticity.

The heater is connected by two heater leads to an electric circuit situated outside of the sensor element. The sensor element is heated to a predefined temperature by applying a predefined heating voltage to the heater in a switched mode. The heating voltage is regulated by determining the temperature-dependent internal resistance of the electrochemical cell.

The insulation layers are made of aluminum oxide, for example, and contain contaminants such as sodium due to the manufacturing process. When a heating voltage is applied, the voltage drop in the heater area may cause mobile ions such as sodium ions to wander within the heating insulation and accumulate on one side of the heater, for example. Due to the polarization of the heater insulation, when the heater is operated in a switched mode (sudden switching on and off of the heater voltage), the heater may inject capacitive interference into the electrochemical cell.

Polarization in the area of the heater insulation also occurs during leak current testing, when a high voltage is applied between the heater and one electrode of the electrochemical cell.

SUMMARY OF THE INVENTION

The sensor element according to the present invention has the advantage over the related art that wandering of ions due to the voltage applied to the heater is prevented.

For this purpose, at least one separating element having a lower porosity than the porous heater insulation is provided between adjacent sections of the wave-form heater. The mobility of ions in a heater insulation having low porosity is substantially lower than within the porous heater insulation. The separating elements thus considerably reduce ion wandering within the heater insulation. At the same time, the heater is embedded in the porous heater insulation and is completely surrounded by the heater insulation, so that cracks in the heater insulation due to high temperature gradients are prevented.

Ion wandering is prevented particularly reliably if the porosity of the separating elements is in the range of 2% to 6% by volume. Adequate elasticity of the heater insulation surrounding the heater is provided by a heater insulation having a porosity of 10% to 20% by volume.

The heater is often used for heating an electrochemical cell. The electrochemical cell is integrated into the layer structure of the sensor element and has a first and a second electrode, as well as a solid electrolyte between the first and the second electrode. If the heater is situated at a distance from the electrochemical cell, there is considerably less heater interference injected into the electrochemical cell than, for example, in the case of a structure in which the heater is situated in a layer between the two electrodes of the electrochemical cell.

If the separating element and the heater insulation are made essentially of the same material, for example, aluminum oxide, proper bonding between the separating element and the heater insulation is ensured.

DETAILED DESCRIPTION

Figure 1:
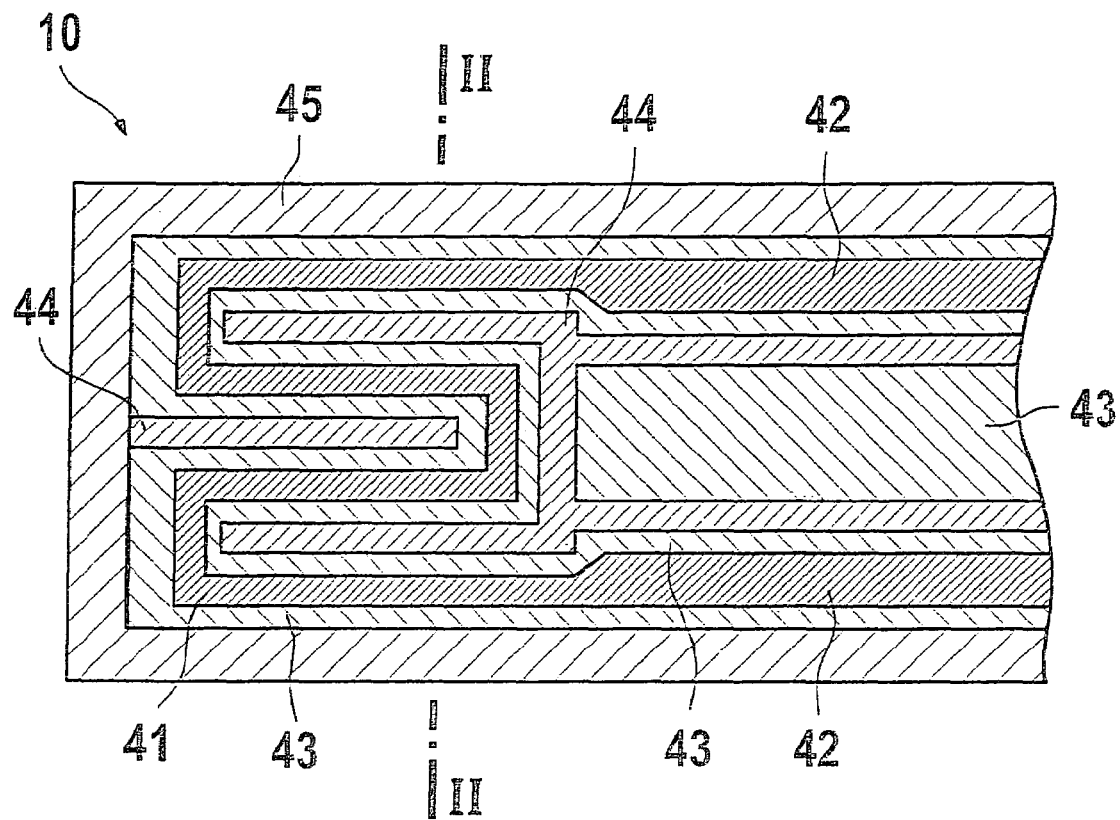
FIG. 1 shows a longitudinal section corresponding to section line I-I in FIG. 2 through the exemplary embodiment of the sensor element according to the present invention.
Figure 2:
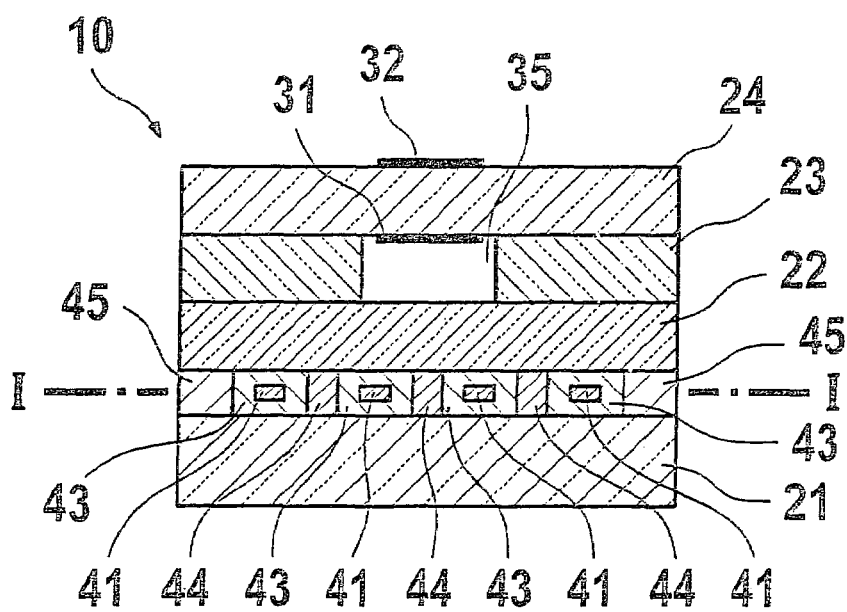
FIG. 2 shows a section corresponding to section line II-II in FIG. 1 perpendicular to the longitudinal axis of the exemplary embodiment of the sensor element according to the present invention.

FIG. 1 and FIG. 2 show as an exemplary embodiment of the present invention, a sensor element 10 having a first solid electrolyte sheet 21, a second solid electrolyte sheet 22, a third solid electrolyte sheet 23, and a fourth solid electrolyte sheet 24.

A reference gas space 35 containing a reference gas is formed in third solid electrolyte sheet 23. For this purpose, reference gas space 35 is connected to the surrounding atmosphere via a channel extending longitudinally through sensor element 10 and an opening on the terminal side. A first electrode 31 is situated in reference gas space 35 on fourth solid electrolyte sheet 24. A second electrode 32 is provided on the external surface of fourth solid electrolyte sheet 24 opposite first electrode 31. First and second electrodes 31, 32 and fourth solid electrolyte sheet 24 in the area of the two electrodes 31, 32 form an electrochemical cell.

A wave-form heater 41 is situated between first and second solid electrolyte sheets 21, 22. Two heater leads 42 connect heater 41 to a circuit (not illustrated), situated outside of sensor element 10, which is able to apply a voltage (heating voltage) between the two heater leads 42. Heater 41 and heater leads 42 are fully surrounded by a porous heater insulation 43. The porosity of heater insulation 43 is approximately 15% by volume. In the layer of heater 41, heater insulation 43 is laterally fully surrounded by a sealing frame 45, which seals heater insulation 43 against the gas surrounding sensor element 10.

Wave-form heater 41 has four sections which extend parallel to the longitudinal axis of sensor element 10. The four sections are connected by three shorter sections perpendicularly to the longitudinal axis of sensor element 10. Separating elements 44 having a porosity of 4% by volume are provided between the adjacent sections of heater 41. Separating elements 44 are also provided between heater lead 42 and between heater lead 42 and a section of heater 41 adjacent to heater lead 42.

Separating elements 44 are at a distance from heater 41, so that separating elements 44 and heater 41 are separated by porous heater insulation 43. Separating elements 44 are situated in such a way that ion wandering between the different sections of heater 41 is prevented. Separating elements 44 are situated in particular in areas in which there is a high voltage differential between two sections of heater 41 when heating voltage is applied, because intensive ion wandering may occur in these areas in particular. Furthermore, ion wandering is enabled by high temperatures. Therefore, it is particularly important that separating elements 44 are provided in the hot areas of sensor element 10, in particular in the area of heater 41.

Heater 41 and heater leads 42 are made of platinum and a ceramic support structure. Porous heater insulation 43 and separating elements 44 are essentially made of aluminum oxide.

In a further exemplary embodiment (not illustrated) of the present invention, the heater is situated in a broadband lambda sensor, which includes an electrochemical pump cell and an electrochemical Nernst cell. The structure and mode of operation of a broadband lambda sensor of this type are described, for example, in German Patent Application No. DE 198 53 601 or in "Automotive Electronics Handbook," $2^{nd}$ Ed., 1999, Publisher: Ronald K.

Jurgen, McGraw-Hill, Section 7, and the documents cited therein.

The present invention is not limited to the form of the heater illustrated in the exemplary embodiment and may be applied to any other forms of the heater. Furthermore, the present invention may be applied to any sensor element having a layered structure and a heater.

What is claimed is:

1. A layered sensor element comprising:
   a porous heater insulation;
   a heater embedded in the porous heater insulation, the heater having two adjacent sections; and
   at least one separating element having a lower porosity than the porous heater insulation, the at least one separating element being situated between the two adjacent sections of the heater.

2. The sensor element according to claim 1, wherein the sensor element is in a gas measuring sensor for measuring a physical property of a measuring gas.

3. The sensor element according to claim 2, wherein the sensor is for determining a temperature of the measuring gas.

4. The sensor element according to claim 2, wherein the sensor is for determining a concentration of a component of the measuring gas.

5. The sensor element according to claim 1, wherein the heater insulation has a porosity in the range of 10% to 20% by volume.

6. The sensor element according to claim 5, wherein the porosity is about 15% by volume.

7. The sensor element according to claim 1, wherein the separating element has a porosity in the range of 0% to 6% by volume.

8. The sensor element according to claim 7, wherein the porosity is about 4% by volume.

9. The sensor element according to claim 1, wherein the separating element and the heater insulation are made substantially of the same material.

10. The sensor element according to claim 9, wherein the material is aluminum oxide.

11. The sensor element according to claim 1, wherein each separating element is situated between the two sections of the heater extending parallel to a longitudinal axis of the sensor element.

12. The sensor element according to claim 1, wherein the separating element is situated in a layer plane of the heater.

13. The sensor element according to claim 1, further comprising at least one electrochemical cell including a first electrode, a second electrode and a solid electrolyte sheet situated between the first and second electrodes, the electrochemical cell being heatable by the heater.

14. The sensor element according to claim 13, wherein the first electrode is situated in a reference gas space, and the second electrode is situated on an external surface of the sensor element.

15. The sensor element according to claim 2, further comprising an electrochemical pump cell and an electrochemical Nernst cell, one electrode of the Nernst cell being situated in a reference gas space and a further electrode of the Nernst cell being situated in a gas space situated in the sensor element, one electrode of the pump cell being situated in the gas space and another electrode of the pump cell being situated on an external surface of the sensor element facing the measuring gas, the gas space being connected to the measuring gas outside of the sensor element via a diffusion barrier.

16. The sensor element according to claim 13, wherein the heater is situated at a distance from the electrochemical cell.

* * * * *